(12) United States Patent
Samaraweera

(10) Patent No.: US 9,398,912 B1
(45) Date of Patent: Jul. 26, 2016

(54) SUTURE REMOVAL TOOL

(71) Applicant: Anura Samaraweera, El Monte, CA (US)

(72) Inventor: Anura Samaraweera, El Monte, CA (US)

( * ) Notice: Subject to any disclaimer, the term of this patent is extended or adjusted under 35 U.S.C. 154(b) by 204 days.

(21) Appl. No.: 14/132,340

(22) Filed: Dec. 18, 2013

Related U.S. Application Data

(60) Provisional application No. 61/739,879, filed on Dec. 20, 2012, provisional application No. 61/813,090, filed on Apr. 17, 2013.

(51) Int. Cl.
  *A61B 17/10* (2006.01)
  *A61B 17/076* (2006.01)

(52) U.S. Cl.
  CPC .................... *A61B 17/076* (2013.01)

(58) Field of Classification Search
  CPC .............. A61F 9/0133; A61B 17/3211; A61B 17/3417; A61B 17/2812; A61B 17/062; A61B 17/10; A61B 18/18; A61B 17/06; A61B 17/28
  See application file for complete search history.

(56) References Cited

U.S. PATENT DOCUMENTS

| | | | | |
|---|---|---|---|---|
| 4,572,185 A | * | 2/1986 | Rich | A61B 17/2812 606/145 |
| 2013/0274743 A1 | * | 10/2013 | Banfalvi | A61B 17/282 606/51 |

* cited by examiner

*Primary Examiner* — Victor Nguyen
(74) *Attorney, Agent, or Firm* — Kenneth L. Green; Averill & Green

(57) ABSTRACT

A suture removal tool grabs, cuts, and removes a suture. The tool includes two arms, a first arm including a single fixed grasping and cutting tip, and the second arm having a fixed cutting tip and a springed grasping tip. When the arms are closed, the grasping and cutting tip of the first arm first contacts the springed grasping tip of the second arm to grasp the suture. As the arms are further closed, the suture is held by the grasping tips, and the cutting tip of the second arm slides past the cutting tip of the first arm, cutting the suture. The cut suture remains grasped between the grasping tips, and may be pulled free. In one embodiment, the suture removal tool is made by cold stamping two mm thick stainless steel, producing burred cutting and/or grasping edges.

19 Claims, 4 Drawing Sheets

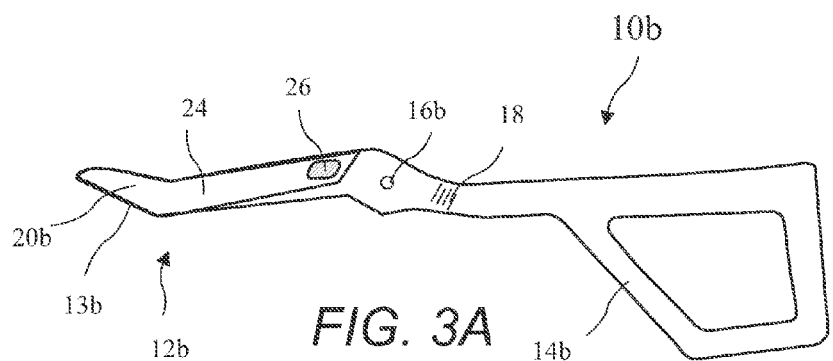
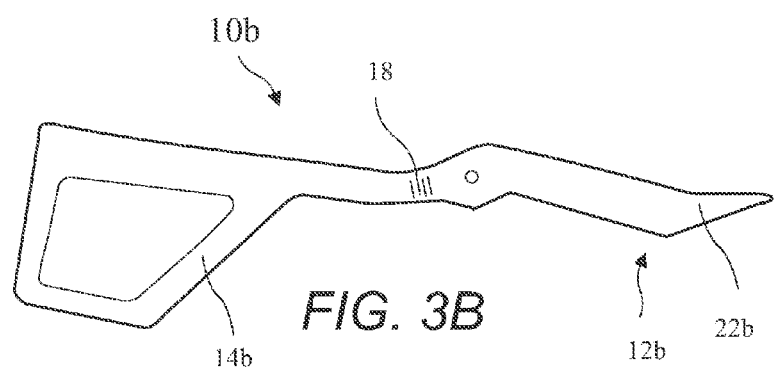
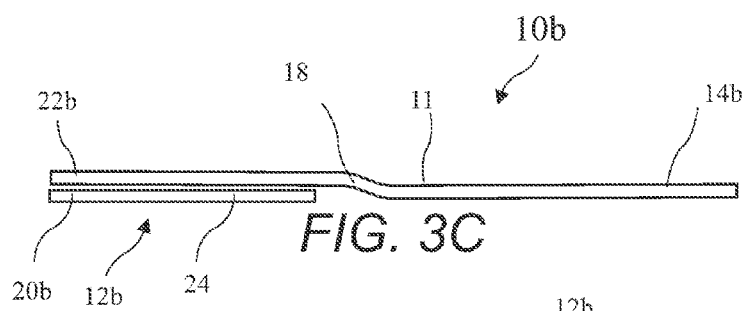
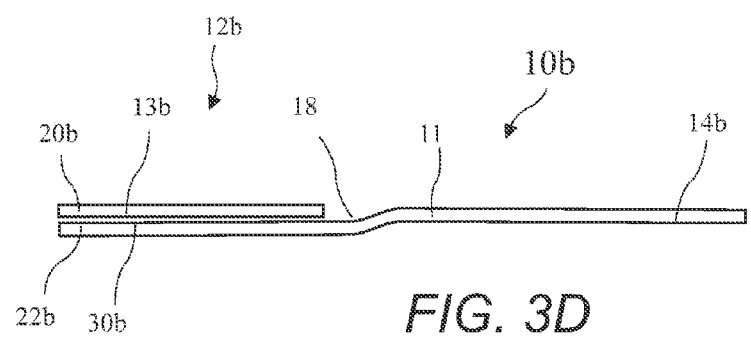

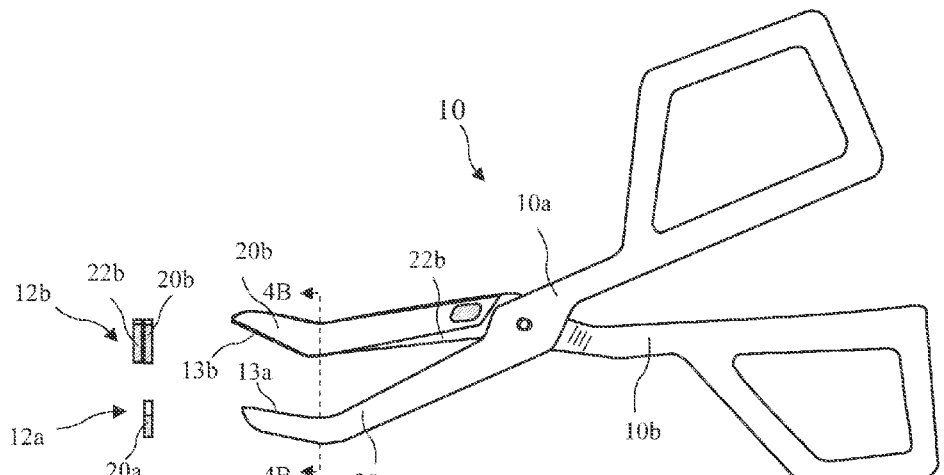
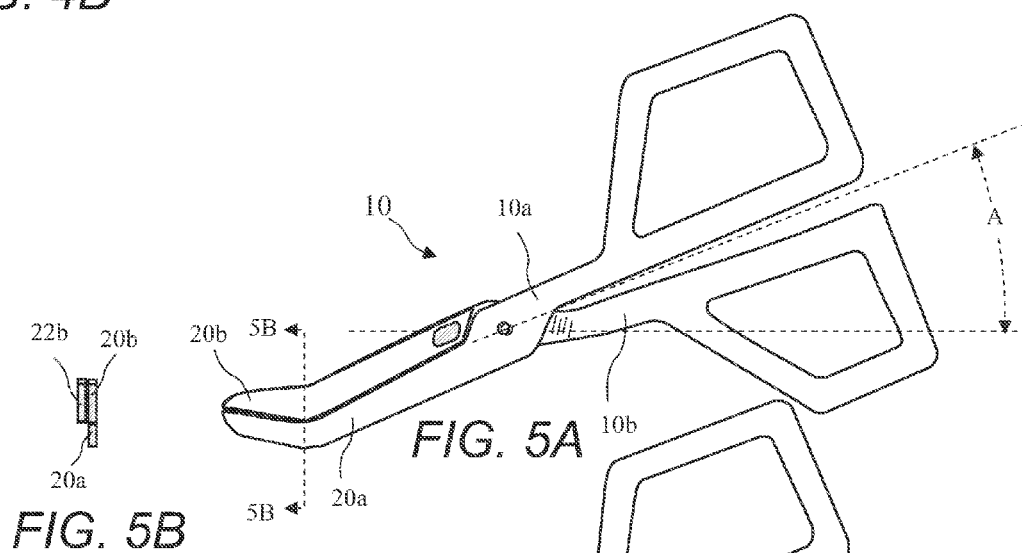
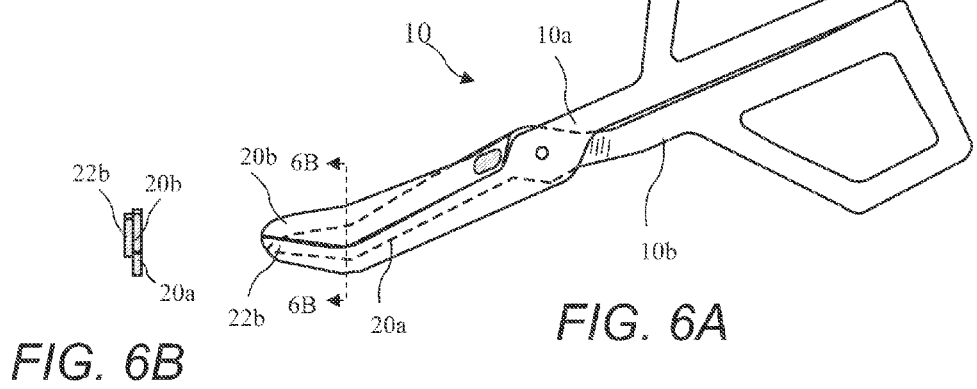

SUTURE REMOVAL TOOL

The present application claims the priority of U.S. Provisional Patent Application Ser. No. 61/739,879 filed Dec. 20, 2012 and U.S. Provisional Patent Application Ser. No. 61/813,090 filed Apr. 17, 2013, which applications are incorporated in its entirety herein by reference.

BACKGROUND OF THE INVENTION

The present invention relates to medical tools and in particular to tools for removing sutures.

Medical procedures often require sutures to close a wound or an incision. Some sutures are absorbable and do not require removal. Other sutures are non-absorbable and are generally removed at some later date. Such removal generally requires that a medical personnel hold a loop of the suture with forceps in one hand, and cut the loop with scissors in another hand. Such two handed suture removal causes patent discomfort because both the forceps and scissors must be inserted between the loop and patient's skin, often resulting in tugging and pulling of the suture even with good coordination of the two hands. Use of both forceps and scissors further requires additional time thus prolonging patient discomfort.

Single apparatus replacing the forceps and scissors have been made, but have not been successful due to cost, impractical designs, and difficulty in use. Thus a need remains for a low cost, practical, and easy to use single tool to replace forceps and scissors for suture removal.

BRIEF SUMMARY OF THE INVENTION

The present invention addresses the above and other needs by providing a suture removal tool which grabs, cuts, and removes a suture. The tool includes two arms, a first arm including a fixed single grasping and cutting tip, and the second arm having a fixed cutting tip and a springed grasping tip. When the arms are closed, the grasping and cutting tip of the first arm first contacts the springed grasping tip of the second arm to grasp the suture. As the arms are further closed, the suture continues to be held by the grasping tips, and the cutting tip of the second arm slides past the cutting tip of the first arm, cutting the suture. The cut suture remains grasped between the grasping tips, and may be pulled free. In one embodiment, the suture removal tool is made by cold stamping two mm thick stainless steel, producing burred cutting and/or grasping edges.

In accordance with one aspect of the invention, there is provided a suture removal tool providing low material cost, simple assembly, small size, inexpensive packaging and distribution, ease of use with only one right or left hand, and reversible cutting direction.

In accordance with one aspect of the invention, there is provided a suture removal tool providing low manufacturing cost. The tool may be made by cold stamping, laser cutting, or water-jet cutting. Such cutting of a stainless steel sheet provides a burred edge on the underside of the cut. The tool is thus manufactured to position the burred edges on opposite edges for grasping a suture and on adjacent edges for cutting the suture, thus eliminating the cost of providing sharpened and or beveled cutting edges.

In accordance with still another aspect of the invention, there is provided a suture removal tool providing reduced patient pain and discomfort. A single tip of the suture removal tool is inserted between a suture loop and the patient's skin in a single movement, thus limiting the tugging or pulling experienced by the use of the traditional forceps and scissors for suture removal. The fact that one end of the suture continues to be held after the cutting action allows this tool to grasp, cut and pull the suture free in one quick movement of one hand of the user while the other hand is available for steadying the wound area to cause the least amount of anxiety, trauma and pain to the patient.

In accordance with another aspect if the invention, the suture removal tool includes a springed grasping tip of the second arm which is made of a suitable plastic material, and portions of handles of both first and second arms, beyond the pivot, are made of a suitable plastic material. In another embodiment, the entire suture removal tool is fabricated out of a suitable plastic material.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 3A is a side view of a lower arm of the suture removal tool according to the present invention.

FIG. 3B is an opposite side view of the lower arm of the suture removal tool according to the present invention.

FIG. 3C is a top view of the lower arm of the suture removal tool according to the present invention.

FIG. 3D is a bottom view of the lower arm of the suture removal tool according to the present invention.

FIG. 4A is a side view of the suture removal tool according to the present invention in an open position.

FIG. 4B is a cross-sectional view of the suture removal tool according to the present invention in the open position, taken along line 4B-4B of FIG. 4A.

FIG. 5A is a side view of the suture removal tool according to the present invention in a grasping position.

FIG. 5B is a cross-sectional view of the suture removal tool according to the present invention in the grasping position, taken along line 5B-5B of FIG. 5A.

FIG. 6A is a side view of the suture removal tool according to the present invention in a cutting position.

FIG. 6B is a cross-sectional view of the suture removal tool according to the present invention in the cutting position, taken along line 6B-6B of FIG. 6A.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figure 1:
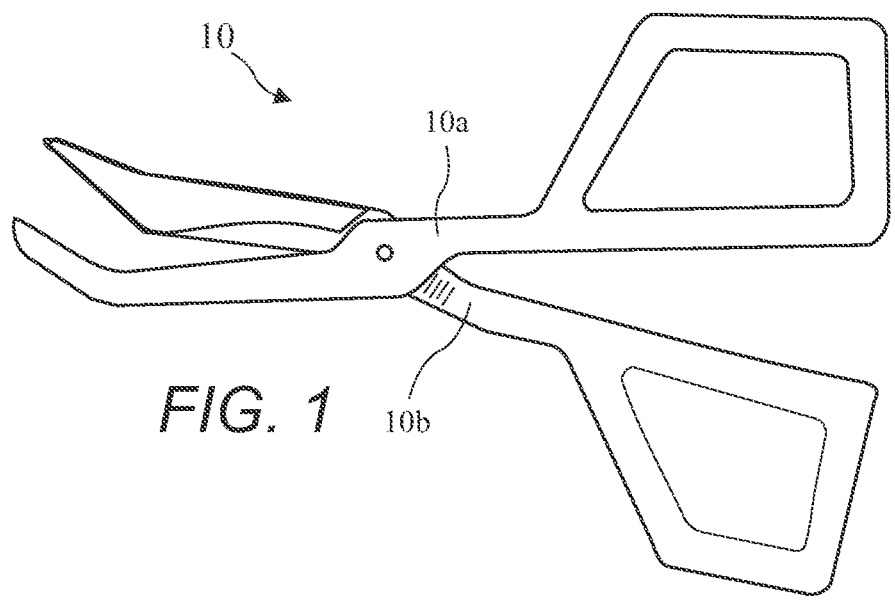
FIG. 1 is a side view of a suture removal tool according to the present invention.

A side view of a suture removal tool 10 according to the present invention is shown in FIG. 1. The suture removal tool 10 comprises a upper arm 10a and a lower arm 10b.

Figure 2A:
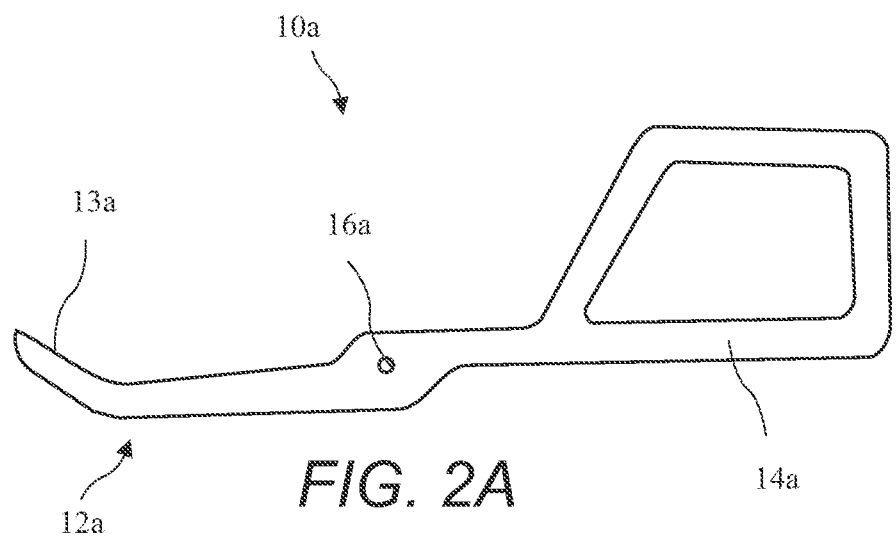
FIG. 2A is a side view of an upper arm of the suture removal tool according to the present invention.
Figure 2B:
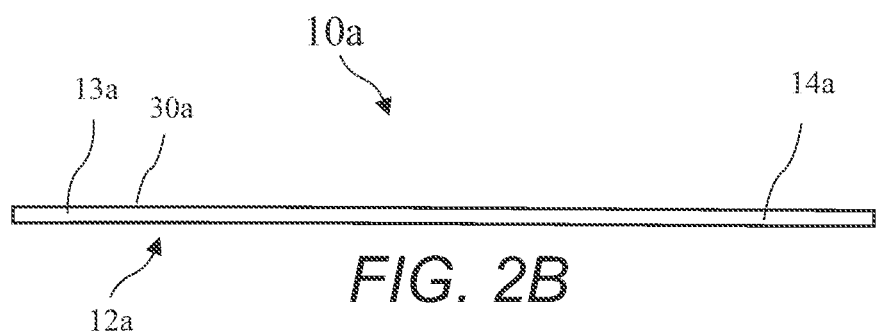
FIG. 2B is a top view of the upper arm of the suture removal tool according to the present invention.

A side view of the upper arm 10a of the suture removal tool 10 is shown in FIG. 2A and a top view of the upper arm 10a is shown in FIG. 2B. The upper arm 10a includes a fixed grasping and cutting end 12a, a handle end 14a, and a pivot axis 16a between the fixed grasping and cutting end 12a and the handle end 14a. The fixed grasping and cutting end 12a preferably includes a first cutting edge 30a (also see FIG. 7) for cooperation with the lower arm 10b. The fixed grasping and cutting end 12a includes a first (or fixed) grasping surface 13a perpendicular to the pivot axis 16a, and the first cutting edge 30a along a side of the grasping surface 13a.

A side view of the lower arm 10b of the suture removal tool 10 is shown in FIG. 3A, an opposite side view of the lower arm 10b is shown in FIG. 3B, a top view of the lower arm 10b is shown in FIG. 3C, and a bottom view of the lower arm 10b is shown in FIG. 3D. The lower arm 10b includes the springed grasping and fixed cutting end 12b, a handle end 14b, and a pivot axis 16b co-axial with the pivot axis 16a and between the springed grasping and fixed cutting end 12b and the handle end 14b. The pivot axes 16a and 16b cooperate allowing opening and closing of the suture removal tool 10, and may be connected by a machine screw, a nut, a rivet, or the like. The lower arm 10b further preferably includes an offset 18 between the pivot axis 16b and the handle end 14b to align handle 14b of the lower arm 10b with the handle 14a of the upper arm 10a.

The springed grasping and fixed cutting end 12b includes a springed grasping tip 20b and a fixed cutting tip 22b. The cutting tip 22b is formed on the lower arm 10b as a fixed extension of the arm 10b, and does not noticeably flex with respect to the lower arm 10b during use. The springed grasping tip 20b is preferably part of a springed cantilevered finger 24 and includes a second (or springed) grasping surface 13b perpendicular to the pivot axis 16b and alignable with the first grasping surface 13a. The springed cantilevered finger 24 has a small cross-section allowing the cantilevered finger 24 to flex after the springed grasping tip 20b contacts the fixed grasping and cutting end 12a. Both the springed grasping tip 20b and the cutting tip 22b preferably include burred edges 30 (see FIG. 7) facing the fixed grasping and cutting end 12a to facilitate grasping and cutting the suture. The springed cantilevered finger 24 is preferably spot welded to a main portion 11 of the lower arm 10b by spot weld 26 or similar attachment.

A side view of the suture removal tool 10 in an open position is shown in FIG. 4A and a cross-sectional view of the suture removal tool in the open position, taken along line 4B-4B of FIG. 4A, is shown in FIG. 4B. In the open position, the fixed grasping and cutting end 12a is separated from the springed grasping and fixed cutting end 12b.

A side view of the suture removal tool 10 in a grasping position is shown in FIG. 5A and a cross-sectional view of the suture removal tool in the grasping position, taken along line 5B-5B of FIG. 5A, is shown in FIG. 5B. In the grasping position, the fixed grasping and cutting tip 20a resides in alignment against the springed grasping tip 20b for grasping a loop of a suture.

A side view of the suture removal tool 10 in a cutting position is shown in FIG. 6A and a cross-sectional view of the suture removal tool in the cutting position, taken along line 6B-6B of FIG. 6A, is shown in FIG. 6B. In the cutting position, the fixed grasping and cutting tip 20a continues to reside in alignment against the springed grasping tip 20b for grasping a loop of a suture, as provided by flexing of the cantilevered finger 24, and the cutting tip 22b is seen to slide past the fixed grasping and cutting tip 20a, thereby cutting the suture grasped between the springed grasping tip 20b and the fixed grasping and cutting tip 20a as described above.

Figure 7:
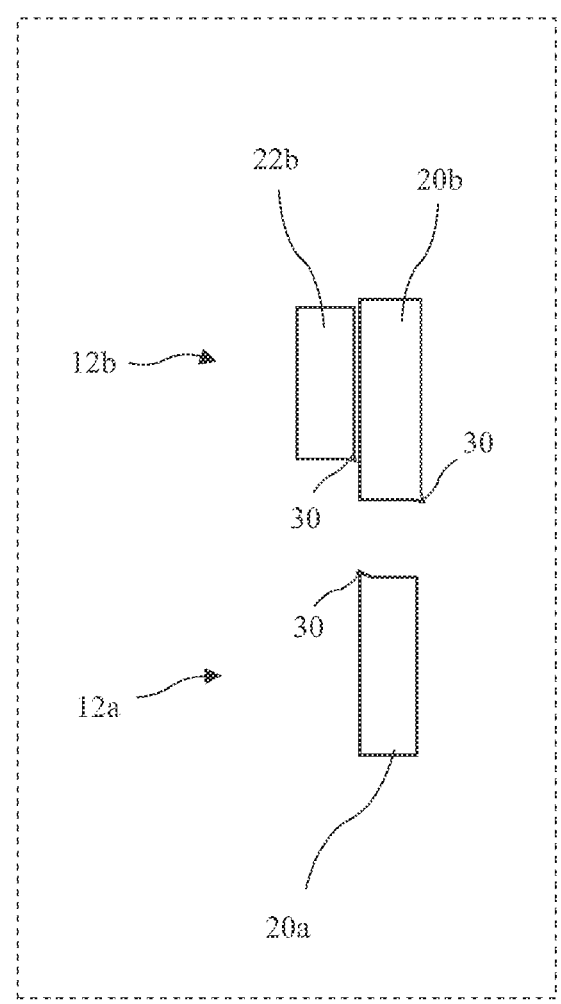
FIG. 7 shows burred cutting and grasping edges according to the present invention.

FIG. 7 shows burrs 30 cutting and grasping edges according to the present invention. Advantageously, the suture removal tool 10 may be made using cold stamping from approximately two mm thick material, for example, two mm thick stainless steel, providing a low cost tool. When the suture removal tool 10 is formed using cold stamping or similar methods, burrs 30 result. The burrs 30 provide non-slip cutting as well as grasping edges for the suture removal tool 10. The suture removal tool 10 may alternatively be made either wholly or partly from plastic providing a very low cost disposable suture removal tool 10.

The suture removal tool 10 with handles angularly offset from the grasping and cutting end at an angle A as shown in FIG. 5A allows easy operation whether the suture removal tool 10 is directed towards or away from a user, and may be used either right or left handed. Such use is an important advantage when working in limited space and because a suture knot may be to the right or left side of the loop.

While the invention herein disclosed has been described by means of specific embodiments and applications thereof, numerous modifications and variations could be made thereto by those skilled in the art without departing from the scope of the invention set forth in the claims.

I claim:

1. A suture removal tool comprising:
an upper arm having;
 a first handle end;
 a fixed grasping and cutting end opposite the first handle end and fixed to the first handle end, the fixed grasping and cutting end including a fixed grasping surface and a first cutting edge along one side of the fixed grasping surface; and
 a first pivot axis between the first handle end and the fixed grasping and cutting end;
a lower arm having:
 a second handle end;
 a springed grasping and fixed cutting end opposite to the second handle end, the springed grasping and fixed cutting end including:
  a springed grasping tip flexibly attached to the lower arm and having a springed grasping surface facing the fixed grasping surface and configured to cooperate with the fixed grasping surface to grasp a suture; and
  a cutting tip fixed to the second handle;
  a second cutting edge along one side of the cutting tip and aligned to slide past the first cutting edge to cut a suture held between the fixed grasping surface and the springed grasping surface; and
 a second pivot axis co-axial with the first pivot axis and between the second handle end and the springed grasping and fixed cutting end, wherein the first and second pivot axes cooperate to open and close the fixed grasping and cutting end and the springed grasping and fixed cutting end, and wherein the first handle end, the fixed grasping and cutting end, the second handle end, and the springed grasping and fixed cutting end, are constrained to pivot in a plane perpendicular to the first and second pivot axes;
in an open position, the fixed grasping and cutting end and the springed grasping and fixed cutting end are separated;
in a grasping position a first grasping surface of the fixed grasping and cutting end is pressed against a second grasping surface of the springed grasping and fixed cutting end and a first cutting edge of the fixed grasping and cutting end is separated from a second cutting edge of the springed grasping and fixed cutting end, thereby configured to grasp but not cut the suture; and in a cutting position, the first grasping surface of the fixed grasping and cutting end remains pressed against the second grasping surface of the springed grasping and fixed cutting end, and the first cutting edge of the fixed grasping and cutting end slides past the second cutting edge of the springed grasping and fixed cutting end, thereby configured to cut the grasped suture allowing the suture to be removed while still grasped between the fixed grasping surface and the springed grasping surface.

2. The tool of claim 1, wherein at least part of the upper arm and the lower arm are made from plastic.

3. The tool of claim 2, wherein the lower arm includes an offset between a handle end and the springed grasping and fixed cutting end, the offset aligning the first grasping surface with the second grasping surface.

4. The tool of claim 1, wherein the suture removal tool is made from stainless steel.

5. The tool of claim 4, wherein the arms are made using cold stamping producing burred edges for cutting the suture.

6. The tool of claim 4, wherein the arms are made using laser cutting producing burred edges for cutting the suture.

7. The tool of claim 4, wherein the arms are made using water-jet cutting producing burred edges for cutting the suture.

8. The tool of claim 4, wherein the lower arm includes an offset between a handle end and the springed grasping and fixed cutting end, the offset aligning the first grasping surface with the second grasping surface.

9. The tool of claim 4, wherein the lower arm is constructed by attaching a springed cantilevered finger including the second grasping surface to a main portion of the lower arm.

10. The tool of claim 1, wherein the entire suture removal tool is fabricated out of a plastic material.

11. The tool of claim 1, wherein portions of handles of both first and second arms, beyond the pivot, are made of a plastic material.

12. The tool of claim 1, wherein a springed grasping tip of the second arm is made of a plastic material.

13. The tool of claim 1, wherein the cutting tip of the springed grasping and fixed cutting end is not noticeably flexible with respect to the lower arm during use.

14. The tool of claim 1, wherein the springed grasping tip of the springed grasping and fixed cutting end is flexible with respect to the lower arm during use.

15. The tool of claim 1, wherein:
in a relaxed position the springed grasping tip of the springed grasping and fixed cutting end resides beside the fixed cutting end of the springed grasping and fixed cutting end; and
in a cutting position the springed grasping tip of the springed grasping and fixed cutting end resides shifted up with respect to the fixed cutting end of the springed grasping and fixed cutting end.

16. A suture removal tool comprising:
an upper arm having;
a first handle end;
a fixed grasping and cutting end opposite the first handle end and fixedly attached to the first handle end to avoid flexing during use, the fixed grasping and cutting end including:
flat, parallel first sides;
a fixed grasping top surface; and
a first cutting edge along one edge of the fixed grasping surface;
a lower arm having:
a second handle end;
a springed grasping and fixed cutting end opposite to the second handle end, the springed grasping and fixed cutting end including:
a cutting tip fixedly attached to the second handle to avoid flexing during use, the cutting tip including:
flat, parallel second sides;
a second cutting edge on an edge of a bottom surface of the cutting tip, the second cutting edge aligned to slide past the first cutting edge to cut a suture held by the suture removal tool; and
a springed grasping tip flexibly attached to the lower arm to allow flexing during use and having a springed grasping bottom surface facing the fixed grasping top surface;
the upper arm and the lower arm pivotable about a common axis to close to a first position wherein the fixed grasping top surface resides against the springed grasping bottom surface to grasp the suture, and the second cutting edge residing above the first cutting edge; and
further closing to a second position wherein the suture is held between the fixed grasping top surface and the springed grasping bottom surface, the springed grasping tip displaced vertically by the closing to the second position, and the second cutting edge residing below the first cutting edge.

17. A suture removal tool comprising:
a rigid upper arm having;
a first handle end;
a fixed grasping and cutting end opposite, and in fixed relationship to the first handle end, the fixed grasping and cutting end including:
a grasping top surface; and
a first cutting edge along one edge of the grasping top surface;
a lower arm having:
a second handle end;
a springed grasping and fixed cutting end opposite to the second handle end, the springed grasping and fixed cutting end including:
a cutting tip in fixed relationship to the second handle, the cutting tip including a second cutting edge on an edge of a bottom surface of the cutting tip, the second cutting edge aligned to slide past the first cutting edge to cut a suture held by the suture removal tool; and
a springed grasping tip attached to the lower arm and residing beside the cutting tip and having a grasping bottom surface facing the grasping top surface;
wherein:
in an open handle position, the grasping bottom surface and the grasping top surface are separated and the second cutting edge is above the first cutting edge;
in a partly closed handle position, the grasping bottom surface and the grasping top surface are pressed together, thereby grasping the suture, and the second cutting edge remains above the first cutting edge; and
in a fully closed handle position, the grasping bottom surface and the grasping top surface are pressed together, thereby grasping the suture, and the springed grasping tip is displaced up with respect to the cutting tip, and the second cutting edge resides below the first cutting edge, thereby cutting the suture held between the grasping top surface and the grasping bottom surface.

18. The tool of claim 17, wherein the upper arm is a single rigid piece and the second handle end and the cutting tip are a single rigid piece.

19. The tool of claim 17, wherein the first handle end and the fixed grasping and cutting end are in a fixed relationship.

\* \* \* \* \*